United States Patent [19]

Gymer

[11] 4,062,966

[45] Dec. 13, 1977

[54] 1-ARYL-2-(1-IMIDAZOLYL) ALKYL ETHERS AND THIOETHERS

[75] Inventor: Geoffrey E. Gymer, Sandwich, England

[73] Assignee: Pfizer Inc., New York, N.Y.

[21] Appl. No.: 676,104

[22] Filed: Apr. 12, 1976

[30] Foreign Application Priority Data

Apr. 30, 1975 United Kingdom ............... 17922/75

[51] Int. Cl.$^2$ ................. C07D 409/12; A61K 31/415
[52] U.S. Cl. ........................ 424/273 R; 260/306.8 R; 548/336; 548/341; 424/270
[58] Field of Search ....................... 260/309; 424/273

[56] References Cited

U.S. PATENT DOCUMENTS

| 3,354,173 | 11/1967 | Godefroi et al. | 260/309 |
| 3,575,999 | 4/1971 | Godefroi et al | 260/309 |
| 3,658,813 | 4/1972 | Godefroi et al. | 260/309 |
| 3,717,655 | 2/1973 | Godefroi et al. | 260/309 |
| 3,732,242 | 5/1973 | Buchel et al. | 260/309 |
| 3,790,594 | 2/1974 | Meiser et al. | 260/309 |
| 3,984,426 | 10/1976 | Winkelmann et al. | 260/309 |
| 3,991,202 | 11/1976 | Janssen et al. | 260/309 |
| 3,992,397 | 11/1976 | Winkelmann et al. | 260/309 |

OTHER PUBLICATIONS

Burger Medicinal Chemistry 2nd ed. pp. 79–81, N.Y., Interscience, 1960.

*Primary Examiner*—Natalie Trousof
*Attorney, Agent, or Firm*—Connolly & Hutz

[57] ABSTRACT

Novel 1-aryl-2-(1-imidazolyl)alkyl ethers and thioethers having anti-fungal properties are disclosed.

18 Claims, No Drawings

1-ARYL-2-(1-IMIDAZOLYL) ALKYL ETHERS AND THIOETHERS

BACKGROUND OF THE INVENTION

This invention relates to certain novel imidazole derivatives. More particularly, it relates to 1-aryl-2-(1-imidazolyl)alkyl ethers and thioethers which possess anti-fungal activity.

SUMMARY OF THE INVENTION

The present invention discloses 1-aryl-2-(1-imidazolyl)alkyl ethers and thioethers having the formula:

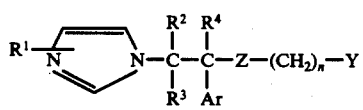 (I)

and the pharmaceutically acceptable acid addition salts thereof wherein $R^1$, $R^2$, $R^3$ and $R^4$ are each hydrogen or alkyl of from 1 to 6 carbon atoms; Ar is phenyl, substituted phenyl, said substituents being halogen, alkyl of from 1 to 6 carbon atoms or alkoxy of from 1 to 6 carbon atoms, thienyl or halothienyl; Z is oxygen or sulfur; n is 1 or 2; and Y is an aromatic heterocyclic group or substituted heterocyclic group, said substituents being halogen, alkyl of from 1 to 6 carbon atoms or alkoxy of from 1 to 6 carbon atoms.

Sub-generic groups of the foregoing compounds which are of interest include those compounds wherein Ar is phenyl or substituted phenyl; Z is oxygen; Z is sulphur; $R^1$, $R^2$, $R^3$, and $R^4$ are each hydrogen; Ar is a 2,4-dichlorophenyl group; n is 1 and Y is a thienyl or halothienyl group.

Also disclosed is a composition in dosage unit form useful for the treatment of fungal infections comprising a pharmaceutical carrier containing from about 10 mg. to 3,000 mg. of a compound of formula (I).

In addition, there is disclosed a method of treating fungal infections in humans comprising administering to a human subject an effective amount of a compound of formula (I).

The terms "lower alkyl" and "lower alkoxy" refer to straight or branch chain groups having from 1 to 6 carbon atoms and halogen means fluorine, chlorine, bromine or iodine.

The preferred lower alkyl and lower alkoxy groups are methyl and methoxy respectively. Ar is preferably a dihalophenyl group, particularly 2,4-dichloro-phenyl. It may also be a 2-chlorothienyl group. Preferred aromatic heterocyclic groups are thienyl, halothienyl and thiazolyl. Preferably $R^1$, $R^2$, $R^3$ and $R^4$ are each hydrogen and n is 1.

Particularly preferred individual compounds of the present invention are 1-[2,4-dichloro-β-(3-thienylmethoxy)phenethyl]imidazole, 1-[2,4-dichloro-β-(5-chloro-2-thienylmethoxy)phenethyl]imidazole, and 1-[2,4-dichloro-β-(2-chloro-3-thienylmethoxy)phenethyl]imidazole. Also preferred are 1-[2,4-dichloro-β-(2-thienylmethoxy)phenethyl]imidazole, 1-[2,4-dichloro-β-(2,5-dichloro-3-thienylmethoxy)phenethyl]imidazole, 1-[2,4-dichloro-β-(5-chloro-2-thienylmethylthio)phenethyl]imidazole, 1-[2,4-dichloro-β-(3-thienylmethylthio)phenethyl]imidazole, 1-[2,4-dichloro-β-(4-thiazolylmethoxy)phenethyl]imidazole and 1-[2-(5-chloro-2-thienyl)-2-(3-chloro-2-thienylmethoxy)ethyl]imidazole.

DETAILED DESCRIPTION OF THE INVENTION

The compounds of formula (I) may be prepared by aralkylation of an appropriate 1-aryl-2-(1-imidazolyl)alkanol or alkane thiol of the formula:

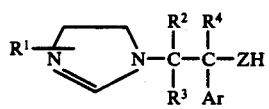 (II)

wherein $R^1$ to $R^4$, Ar and Z are as previously defined.

Such a reaction comprises converting the alcohol or thiol of formula (II) to its alkali metal derivative by treatment with a strong base, such as an alkali metal amide or hydride, and reacting with the appropriate aralkyl halide of the formula:

 (III)

where n and Y are as previously defined and X is a halogen atom, preferably chlorine.

Suitable solvents for the aralkylation are the aromatic hydrocarbons, e.g. benzene, toluene or xylene; ethers, e.g. tetrahydrofuran or 1,2-dimethoxyethane; or dimethylformamide. Tetrahydrofuran is a preferred solvent. The reaction may be performed at a temperature between 0° C and the reflux temperature of the solvent and may take from 1 to 24 hours depending on the temperature and the particular nature of the solvent and reactants employed. The product is conveniently isolated by adding water to the reaction mixture and extracting with ether. The product may then be purified as the free base or converted to a salt, e.g. the hydrochloride, and purified by recrystallization.

The compounds of formula (I) may also be prepared by the aralkylation of a compound of formula:

 (IV)

wherein Z, n and Y are as previously defined.

Such a reaction comprises converting the alcohol or thiol of formula (IV) to its alkali metal derivative by treatment with a strong base, such as an alkali metal amide or hydride and reacting with an appropriate 1-(β-halo-aryl-ethyl)imidazole derivative of the formula:

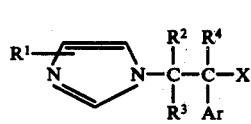 (V)

wherein $R^1$ to $R^4$ and Ar are as previously defined and X is a halogen atom, preferably chlorine.

Suitable solvents for the aralkylation are aromatic hydrocarbons, e.g. benzene, toluene or xylene; or ethers, e.g. tetrahydrofuran or 1,2-dimethoxyethane; or dimethylformamide. Tetrahydrofuran is a preferred solvent. The reaction may be performed at a temperature between 0° C and the reflux temperature of the solvent and may take from 1 to 24 hours depending on the particular nature of the solvent and reactants employed. It has been found, however, that in the case of the thiols of formula (IV) the reaction is generally complete within 3 hours at room temperature when performed in tetrahydrofuran. The product may be isolated as the free base or a salt as previously described.

The starting alcohols of formula II where Z is O are known compounds described in British Patent No. 1,244, 530. The starting halides of formula (V) are described in U.S. Pat. No. 3,679,697. The halides of formula (III) and the compounds of formula (IV) are generally known compounds readily accessible or they may be prepared by conventional methods. Thus, for example, the thenyl halides of formula (III) (when Y is a thiophene ring and $n$ is 1) are prepared, according to literature methods, by reaction of a methyl-thiophene derivative with N-bromosuccinimide, or by chloromethylation of thiophene or an appropriate halothiophene with formaldehyde and concentrated hydrochloric acid. The thiols of formula (IV) (where Z is S) may be prepared from the halides of formula (III) by reaction with thiourea followed by hydrolysis of the intermediate thiouronium derivative by refluxing with 10% sodium hydroxide solution.

Thiols of formula (II) where Z is S may also be prepared by known methods, for example they may be prepared from the chloro compounds of formula (V) by reaction with thiourea followed by hydrolysis of the resulting thiouronium derivative.

The compounds of the invention exist in D- and L-optically active isomeric forms and the invention includes these forms as well as the racemic mixtures. The racemic products may be resolved by well known techniques, for example by fractional crystallization of an addition salt formed with an optically active acid.

Pharmaceutically acceptable acid addition salts of the compounds of the invention are those formed from acids which form non-toxic acid addition salts containing pharmaceutically acceptable anions, such as the hydrochloride, hydrobromide, sulfate or bisulfate, phosphate or acid phosphate, acetate, maleate, fumarate, lactate, tartrate, citrate, gluconate, succinate and p-toluenesulphonate salts.

The compounds of the invention and their pharmaceutically acceptable acid addition salts are anti-fungal agents, useful in combatting fungal infections in animals, including humans. For example they are useful in treating topical fungal infections in man cuased by species of Candida, Trichophyton or Epidermophyton, or in mucosal infections caused by *Candida albicans* (e.g. thrush and vaginal candidiasis). They may also be used systemically in the treatment of systemic fungal infections caused by for example *Candida albicans* or *Cryptococcus neoformans*.

The in vitro evaluation of the anti-fungal activity of the compounds has been performed by determining the minimum inhibitory concentration (m.i.c.) of the test compounds in a suitable medium at which growth of the particular micro-organism fails to occur. In practice a series of agar plates, each having the test compound incorporated at a particular concentration are inoculated with a standard culture of *Candida albicans* and each plate is then incubated for 24 hours at 37° C. The plates are then examined for the presence or absence of growth of the fungus and the appropriate m.i.c. value is noted. Other microorganisms used in such tests have included *Cryptococcus neoformans, Aspergillus fumigatus, Trichophyton rubrum, Epidermophyton floccosum, Coccidioides immitis,* and *Torulopsis glabrata.*

The in vivo evaluation of the compounds has also been carried out at a series of dose levels by intraperitoneal or intravenous injection or by oral administration, to mice which are inoculated with a strain of *Candida albicans.* Activity is based on the survival of a treated group of mice after the death of an untreated group of mice following 48 hours observation. The dose level at which the compound provides 50% protection against the lethal effect of the infection is noted.

For human use, the anti-fungal compounds of the invention can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules either along or in admixture with excipients, or in the form of elixirs or suspensions containing flavoring or coloring agents. They may be injected parenterally, for example, intravenously, intramuscularly or subcutaneously. For parenteral administration, they are best used in the form of a sterile solution which may contain other substances, for example, enough salts or glucose to make the solution isotonic.

For oral and parenteral administration to human patients, it is expected that the daily dosage level of the anti-fungal compounds of the invention will be comparable with that of anti-fungal agents currently in use, e.g. from 0.5 to 50 mg/kg (in divided doses) when administered by the parenteral routes, or from 2 to 200 mg/kg (in divided doses) when administered by the oral route. Thus tablets or capsules of the compounds can be expected to contain from 30 mg to 3 g of active compound for administration orally up to 4 times a day, while dosage units for parenteral administration will contain from 10 mg to 1 g of active compound. The physician in any event will determine the actual dosage which will be most suitable for an individual patient and it will vary with age, the weight and response of the particular patient. The above dosages are exemplary of the average host. There can, of course, be individual cases where higher or lower dosage ranges are merited, and such are within the scope of this invention.

Alternatively, the anti-fungal compounds of formula (I) may be administered in the form of a suppository or pessary or they may be applied topically in the form of a cream, ointment or dusting powder. For example, they may be incorporated into a cream consisting of an aqueous emulsion of polyethylene glycols or liquid petrolatum; or they may be incorporated, at a concentration between 1 and 10%, into an ointment consisting of a white wax or white soft petrolatum base together with such stabilizers and preservatives as may be required.

EXAMPLE 1

A solution of 1-(2,4-dichloro-phenyl)-2-(1-imidazolyl) ethanol (1.5 g, 5.8mmole) dissolved in dry tetrahydrofuran (10 ml) was added to a stirred suspension of sodium hydride (0.39 g, as 80% dispersion in oil, 16 mmole) in dry tetrahydrofuran (10 ml) and warmed to 70° C for 90 minutes. The mixture was cooled in ice and a solution of 2-chloromethyl-thiophene (1.16 g, 8.8 mmole) in dry tetrahydrofuran was added. The mixture was heated at 70° for 3 hours and allowed to stir at room temperature overnight. The solvent was removed under vacuum and the residue stirred with dry ether (200 ml). The ether solution was filtered through celite and saturated with hydrogen chloride gas to precipitate an oil which was solidified by trituration with ether and ethylacetate. The solid product was collected and recrystallized from a mixture of acetone and di-isopropyl ether to give 1-[2,4-dichloro-β-(2-thienylmethoxy)phenethyl]imidazole hydrochloride as fine white crystals (0.63 g, 31%) m.p. 153°-154° C. (Found: C, 49.2; H, 3.8; N, 7.3. $C_{16}H_{14}Cl_2N_2OS \cdot HCl$ requires C, 49.3; H, 3.9; N, 7.2%).

EXAMPLES 2 to 8

The following compounds were prepared by the general method described in Example 1, starting with 1-(2,4-dichloro-phenyl)-2-(1-imidazolyl)ethanol and the appropriate bromo or chloromethylthiophene derivative. Table I shows the compounds prepared, together with their melting points and analytical data. The structures were also confirmed by IR and NMR spectroscopy.

| Ex. | Y | m.p. | Analysis % (Theoretical in brackets) |
|---|---|---|---|
| 2 | 2-thienyl | 123-124* | C, 49.3 H, 3.9 N, 7.4 (C, 49.3 H, 3.9 N, 7.1) |
| 3 | 5-chloro-2-thienyl | 177-181* | C, 41.9 H, 2.8 N, 6.5 (C, 41.9 H, 2.9 N, 6.1) |
| 4 | 5-chloro-3-thienyl | 164-167* | C, 45.0 H, 3.4 N, 6.9 (C, 45.3 H, 3.4 N, 6.6) |
| 5 | 5-chloro-2-thienyl | 142-144* | C, 43.3 H, 3.4 N, 6.4 *(C, 43.4 H, 3.6 N, 6.3) |
| 6 | 2,5-dibromo-3-thienyl | 168-170* | C, 35.1 H, 2.4 N, 5.2 (C, 35.1 H, 2.4 N, 5.1) |
| 7 | 2,3,5-trichloro-thienyl | 187-190* | C, 39.1 H, 2.5 N, 5.9 (C, 39.0 H, 2.5 N, 5.7) |
| 8 | 3-chloro-5-bromo-thienyl | 191-193* | C, 37.9 H, 2.8 N, 5.7 +(C, 37.5 H, 2.8 N, 5.5) |

(Structure above table: $N \equiv N - CH_2 - CH - O - CH_2 - Y \cdot HCl$ with 2,4-dichlorophenyl group on the CH)

*Hydrate
+Hemihydrate

EXAMPLE 9

A solution of 3-mercaptomethyl-thiophene (3.33 g, 0.019 mole) dissolved in dry tetrahydrofuran (6 ml) was added to a suspension of sodium hydride (1.7 g, as an 80% dispersion in oil, 0.057 mole) in dry tetrahydrofuran (40 ml). After stirring for 1 hour at room temperature the mixture was cooled to 0° C and 1-(β-chloro-2,4-dichloro-phenethyl)imidazole (5.0 g, 0.16 mole) was added in portions over a period of 1 hour. The solution was stirred at 0° C for 90 minutes then diluted with water (400 ml) and extracted with ether (3 × 100 ml). The combined ether extracts were treated with HCl gas, the solvent evaporated and the residue taken up in water. The aqueous solution was washed with ether and then basified and extracted with ether. The ether extracts were dried and the solvent removed. The residue was converted to the hydrochloride salt with ethereal HCl and the product recrystallized from a mixture of methanol and di-isopropyl ether to give 1-[1,4-dichloro-β-(3-thienylmethylthio)phenethyl]imidazole hydrochloride (2.5 g, 38%), m.p. 139°-141° C. (Found: C, 46.8; H, 3.7; N, 6.8. $C_{16}H_{14}N_2Cl_2S_2 \cdot HCl$ requires C, 47.4; H, 3.7; N, 6.9%).

EXAMPLE 10

In a similar manner to that described in Example 9, but using 5-chloro-2-mercaptomethyl-thiophene as starting material, was prepared 1-[2,4-dichloro-β-(5-chloro-2-thienylmethylthio) phenethyl]imidazole hydrochloride m.p. 140°-143°. (Found: C, 43.4; H, 3.1; N, 6.0. $C_{16}H_{13}N_2Cl_3S_2 \cdot HCl$ requires C, 43.8; H, 3.2; N, 6.4%).

EXAMPLE 11

A solution of 1-(2,4-dichloro-phenyl)-2-(1-imidazolyl) ethanol (2.4 g, 9.4 mmole) in dry tetrahydrofuran (20 ml) was added to sodium hydride (0.62 g, as an 80% dispersion in oil, 0.02 mole) and warmed at 70° C for 90 minutes. The solution was cooled to 0° C and 4-chloromethylthiazole (1.5 g, 11.2 mmole), dissolved in a little dry tetrahydrofuran, was added. The mixture was stirred at 0° C for 1 hour and at room temperature for 6 hours. Further 4-chloromethylthiazole (0.25 g) was added and the stirring continued for 36 hours. The reaction mixture was then diluted with water (70 ml) and extracted several times with ether. The ether extracts were combined, dried over $MgSO_4$ and evaporated. The oily residue was taken up in dry ether (50 ml) and treated with a solution of HCl in ether. The solid precipitate was collected and recrystallized from a mixture of methanol and di-isopropyl ether to give 1-[2,4-dichloro-β-(4-thiazolylmethoxy) phenethyl]imidazole hydrochloride (1.7 g, 46%) m.p. 183°-184°. (Found: C, 46.3; H, 3.7; N, 10.7. $C_{15}H_{13}N_3Cl_2OS \cdot HCl$ requires C, 46.1; H, 3.6; N, 10.7%).

EXAMPLE 12

In the same manner as described in Example 11, but using 2-chloromethyl-thiazole as starting material, was prepared 1-[2,4-dichloro-β-(2-thiazolylmethoxy)phenethyl]imidazole hydrochloride. The product was obtained as a hygroscopic gum but was shown to be homogeneous by T.L.C. and the structure confirmed by IR and NMR spectroscopy.

EXAMPLE 13

A solution of 1-(5-chloro-2-thienyl)-2-(1-imidazolyl) ethanol (1.1 g, 4.8 mmole) dissolved in dry tetrahydrofuran (10 ml) was added to a stirred suspension of sodium hydride (0.4 g, as 80% dispersion in oil, 16 mmole) in dry tetrahydrofuran (40 ml). After stirring for 1 hour at room temperature the mixture was cooled in ice and a solution of 2-bromomethyl-3-chloro-thiophene (1.0 g, 4.7 mmole) in dry tetrahydrofuran (10 ml) was added dropwise. The mixture was allowed to stir for a further 1 hour at 15° C and the solvent then removed under vacuum. The residue was extracted several times with diethyl ether and the etheral extracts were combined and evaporated. The residue was taken up in a little diethyl ether and treated with a solution of hydrogen chloride in diethyl ether to precipitate a gum which solidified on trituration with acetone and ether. Recrystallization from a mixture of acetone, methanol and diisopropyl ether gave 1-[2-(5-chloro-2-thienyl)-2-(3-chloro-2-thienyl methoxy)ethyl]imidazole hydrochloride as a white solid (0.5 g, 32%) m.p. 120°–121° C. (Found: C, 41.6; H, 3.35; N, 6.9. $C_{14}H_{12}N_2Cl_2OS_2 \cdot HCl$ requires C, 42.5; H, 3.3; N, 7.1%).

EXAMPLE 14

The following illustrate pharmaceutical compositions according to the invention for the treatment of fungal infections. Parts are by weight.

1. Capsule: 71 parts of 1-[2,4-dichloro-β-(2-chloro-3-thienylmethoxy)phenethyl]imidazole hydrochloride are granulated with 3 parts of maize starch and 22 parts lactose and then a further 3 parts of maize starch and 1 part magnesium stearate are added and the mixture is regranulated and filled into capsules.
2. Cream: 2 parts of 1-[2,4-dichloro-β-(2-chloro-3-thienylmethoxy)phenethyl]imidazole hydrochloride are dissolved in 10 parts of propylene glycol or a low molecular weight polyethylene glycol and mixed into 88 parts of a vanishing cream base.
3. Dusting Powder: 2 parts of 1-[2,4-dichloro-β-(2-chloro-3-thienylmethoxy)phenethyl]imidazole hydrochloride are ground with 9 parts of maize starch and then 89 parts of talcum powder are added and grinding continued until the required consistency is obtained.
4. Pessary: 2 parts of 1-[2,4-dichloro-β-(2-chloro-3-thienylmethoxy)phenethyl]imidazole hydrochloride are suspended in 98 parts of a warm liquefied suppository base which is poured into moulds and allowed to cool.

EXAMPLE 15

The compounds prepared in Examples 1 to 13 have been tested for anti-fungal activity by the methods previously described and the m.i.c. values against *Candida albicans* are given below.

| In Vitro Activity vs. *Candida Albicans* | |
|---|---|
| Example | m.i.c. (µg/ml) |
| 1 | 6.2 |
| 2 | 6.2 |
| 3 | 6.2 |
| 4 | 6.2 |
| 5 | 12.5 |
| 6 | 12.5 |
| 7 | 12.5 |
| 8 | 3.1 |
| 9 | 12.5 |
| 10 | 12.5 |
| 11 | 25 |
| 12 | 50 |
| 13 | 3.1 |

A number of the compounds were also tested against several other microorganisms and the results are as follows:

| In Vitro Activity vs: Various Microorganisms | | | | | |
|---|---|---|---|---|---|
| | m.i.c. (µg/ml) | | | | |
| Example | Trichophyton rubrum | Epodermophyton floccosum | Aspergillus fumigatus | Cryptococcus neoformans | Coccidioides immitis |
| 1 | 3.2 | 3.2 | 12.5 | 12.5 | 12.5 |
| 2 | 0.8 | 3.2 | 6.2 | 3.1 | 3.2 |
| 4 | 0.8 | 0.8 | 3.1 | 3.1 | 1.6 |
| 5 | 3.1 | 6.2 | 12.5 | 0.8 | 12.5 |
| 11 | 3.1 | 6.2 | 25 | <0.4 | 25 |

What is claimed is:

1. A 1-aryl-2-(1-imidazolyl)alkyl ether or thioether having the formula:

and the pharmaceutically acceptable acid addition salts thereof wherein $R^1$, $R^2$, $R^3$ and $R^4$ are each hydrogen or alkyl of from 1 to 6 carbon atoms; Ar is phenyl, substituted phenyl, said substituents being halogen, alkyl of from 1 to 6 carbon atoms or alkoxy of from 1 to 6 carbon atoms, thienyl or halothienyl; Z is oxygen or sulfur; $n$ is 1 or 2; and Y is thienyl or substituted thienyl group, said substituents being halogen, alkyl of from 1 to 6 carbon atoms or alkoxy of from 1 to 6 carbon atoms.
2. A compound as claimed in claim 1 in which Ar is phenyl or substituted phenyl.
3. A compound as claimed in claim 1 in which Z is oxygen.
4. A compound as claimed in claim 1 in which Z is sulfur.
5. A compound as claimed in claim 1 in which $R^1$, $R^2$, $R^3$ and $R^4$ are each a hydrogen atom.
6. A compound as claimed in claim 2 in which Ar is a 2,4-dichlorophenyl group.
7. A compound as claimed in claim 1 in which $n$ is 1.
8. A compound as claimed in claim 1 in which Y is a thienyl or halothienyl group.
9. 1-[2,4-dichloro-β-(3-thienylmethoxy)phenethyl]-imidazole.
10. 1-[2,4-dichloro-β-(5-chloro-2-thienylmethoxy)-phenethyl]imidazole.
11. 1-[2,4-dichloro-β-(2-chloro-3-thienylmethoxy)-phenethyl]imidazole.
12. 1-[2,4-dichloro-β-(2-thienylmethoxy)phenethyl]-imidazole.
13. 1-[2,4-dichloro-β-(2,5-dichloro-3-thienylmethoxy)phenethyl]imidazole.
14. 1-[2,4-dichloro-β-(5-chloro-2-thienylmethylthio)-phenethyl]imidazole.
15. 1-[2,4-dichloro-β-(3-thienylmethylthio)phenethyl]imidazole.
16. 1-[2-(5-chloro-2-thienyl)-2-(3-chloro-2-thienylmethoxy)ethyl] imidazole.
17. A composition in dosage unit form useful for the treatment of fungal infections comprising a pharmaceutical carrier containing from about 10 mg. to about 3,000 mg. of a compound as claimed in claim 1.
18. A method of treating fungal infections in animals which comprises parentally or orally administering to an animal in need of such treatment an antifungal effective amount of a compound as claimed in claim 1.

* * * * *

UNITED STATES PATENT AND TRADEMARK OFFICE
CERTIFICATE OF CORRECTION

PATENT NO. : 4,062,966
DATED : DECEMBER 13, 1977
INVENTOR(S) : GEOFFREY E. GYMER

It is certified that error appears in the above-identified patent and that said Letters Patent are hereby corrected as shown below:

Column 2, line 10, the formula should read:

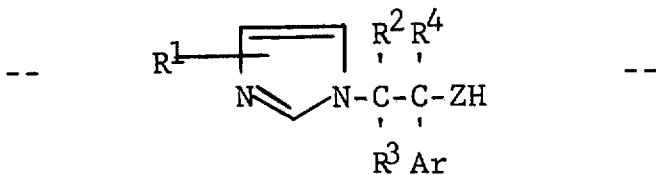

Signed and Sealed this

Eleventh Day of April 1978

[SEAL]

Attest:

RUTH C. MASON
*Attesting Officer*

LUTRELLE F. PARKER
*Acting Commissioner of Patents and Trademarks*